United States Patent [19]

Anderson

[11] 4,330,271
[45] May 18, 1982

[54] ORTHODONTIC-DISPENSER AND TOOL COMBINED WITH DISPENSED ARTICLES

[75] Inventor: Roland M. Anderson, Portland, Oreg.

[73] Assignee: Modcom, Inc., Canby, Oreg.

[21] Appl. No.: 224,383

[22] Filed: Jan. 12, 1981

[51] Int. Cl.³ .............................................. A61C 7/00
[52] U.S. Cl. ......................................... 433/3; 433/18; 433/19
[58] Field of Search .......................... 433/18, 13, 2, 3; 29/413; 81/302

[56] References Cited

U.S. PATENT DOCUMENTS

| 3,530,583 | 9/1970 | Klein et al. | 433/18 |
| 4,038,753 | 8/1977 | Klein | 433/18 |
| 4,106,374 | 6/1978 | Dragan | 81/302 |
| 4,167,063 | 9/1979 | Sosnzy | 433/3 |
| 4,217,686 | 8/1980 | Dragan | 29/413 |

Primary Examiner—Robert Peshock
Attorney, Agent, or Firm—Kolisch, Hartwell & Dickinson

[57] ABSTRACT

A patient-usable orthodontic device for carrying, dispensing and installing intraoral tension-applying devices of the type including a pair of spaced endless loops which are intended for catching onto spaced hooks secured to tooth bands or the like in a patient's mouth. The device includes a molded elastomer portion having a body, and a plurality of tension-applying devices severably joined to the body. Formed in the body is a projecting finger, the outer end of which carries a rigid catch designed to aid in the installation of a tension-applying device which has been severed from the body.

2 Claims, 4 Drawing Figures

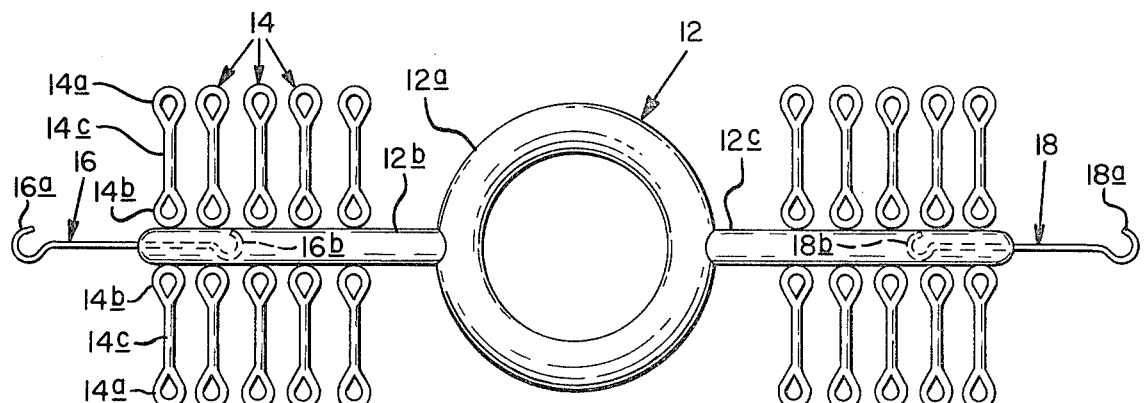
FIG. 1
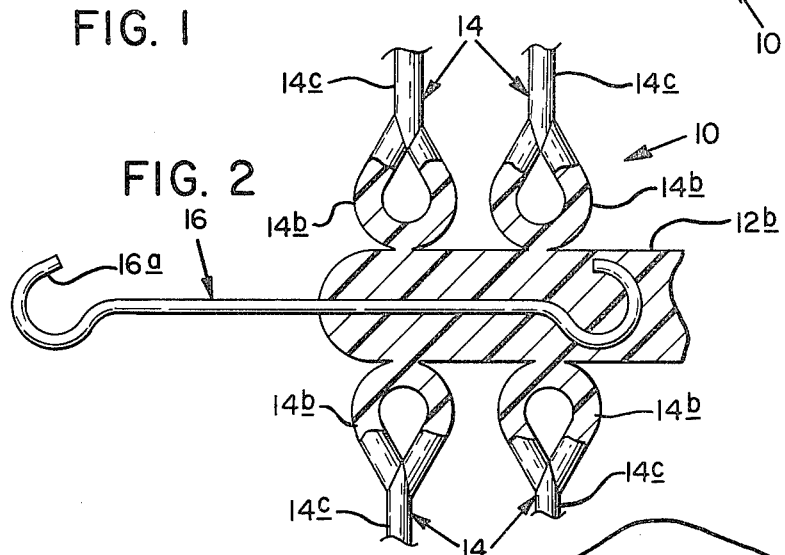
FIG. 2
FIG. 3
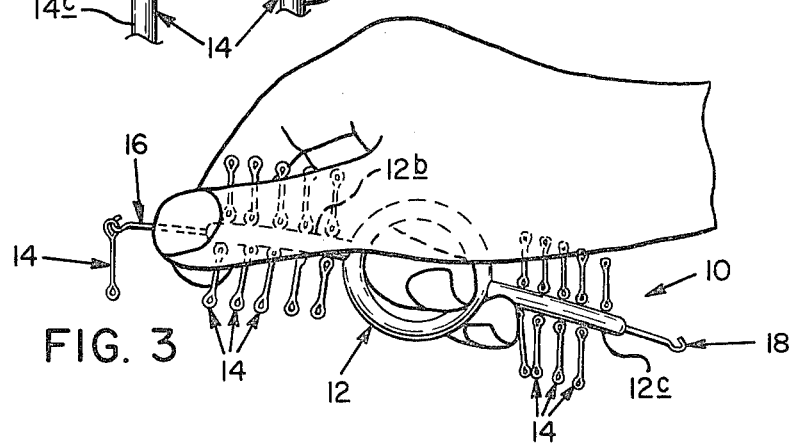
FIG. 4
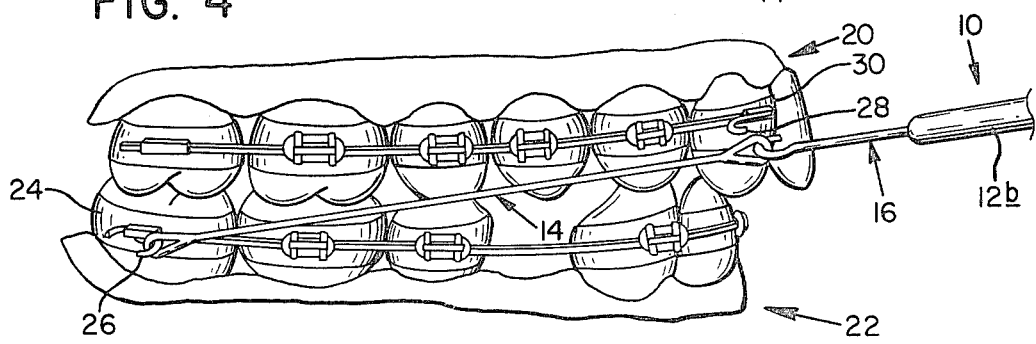

ORTHODONTIC-DISPENSER AND TOOL COMBINED WITH DISPENSED ARTICLES

BACKGROUND AND SUMMARY OF THE INVENTION

This invention relates to an orthodontic device, and more particularly, to a patient-usable device for carrying, dispensing, and installing replaceable intraoral tension-applying devices.

There are many situations in orthodontic treatment wherein it is necessary to apply tension forces between two relatively widely spaced locations in a person's mouth. These locations may either be intramaxillary (i.e., located along the same jaw). Or intermaxillary (i.e., distributed between the two jaws). An illustration of the latter kind of situation is an upper jaw overbite case in which an orthodontist decides to apply tension to pull the upper jaw rearwardly relative to the lower jaw to align them, in a fore-and-aft sense, more favorably.

It is a relatively common practice today to apply such a tension force utilizing a molded elastomer having an elongated shape with its opposite ends substantially defined by a pair of eyelets, and with an elastomeric strand extending between and joining these eyelets. In an operative condition, the eyelets are caught on hooks which have been placed by the orthodontist at the desired locations in a person's mouth, and the hooks are located so that when the device is in place, the strand between the eyelets is stretched, and thus tensed to apply the desired corrective force.

Whereas modern-day elastomeric ligatures that are used to tie an arch wire to brackets (or the like) mounted within a person's mouth, after installation, and until replacement, are relatively static in nature, tension-applying devices for the kind of purpose like that expressed above experience quite a bit of dynamic movement after installation. For example, where such a device is used in an intermaxillary setting, the device is tensed and relaxed recurrently and over widely different limits each time that a person makes a jaw movement in his mouth. Accordingly, these devices have relatively short useful life spans, and must be replaced at frequent intervals.

In the past, it has been a practice for an orthodontist to supply a patient with an extra supply of tension-applying devices like the one which he has originally installed, with instructions to replace the same at certain minimum time intervals, or whenever breakage occurs. Unfortunately, patients, who are often quite young, are not reliable replacers of expended or broken elastomer devices, and even with respect to those who are, they experience some inconvenience and difficulty in installing a new device properly.

A general object of the present invention is to facilitate patient attendance to an orthodontist's instructions to replace tension-applying devices of the type generally mentioned.

Proposed according to a preferred embodiment of the invention is a unitary apparatus having a molded portion with a body which acts as a carrier for a plurality of severably joined (integrally molded) tension-applying devices of the type generally outlined above. Each of these devices, in general terms, has an elongated configuration, with eyelets formed at opposite ends interconnected by an elastomeric strand. Included in the molded portion of the device is an elongated finger, the outer end of which carries a relatively rigid catch which can be used to facilitate placement and installation of a replacement tension-applying device in a person's mouth.

In actual operation, when it is necessary to replace a tension-applying device, a fresh one of these devices is broken away from the body of the apparatus, with an eyelet therein then caught over the catch in the device. With the apparatus held in the patient's hands, it then becomes a relatively easy proposition for him to place the opposite or free end of the severed tension-applying device at one of the hook locations in the mouth where it is intended to be hooked, with the apparatus, thereafter through pulling on the finger, used to stretch the tension-applying device into a condition enabling ready placement of the other end at the other hook location in the mouth.

A number of advantages are offered by the apparatus of the invention. To begin with, what a patient leaves an orthodontist's office with is a unitary product, rather then an aggregation of separate replacement pieces which can easily be dispersed and lost. Secondly, the apparatus of the invention is constructed to act as its own dispenser and installation tool for a tension-applying device which is severed from the main body in the apparatus. This construction greatly minimizes the specific dexterity which is required of a patient in replacing a device. Finally, the use of the main body in the apparatus, and its catch, to stretch a replacement tension-applying device into place, overcomes the difficulty which many young people have in finger-stretching a replacement device sufficiently to enable hooking of its opposite ends in place.

These and other objects and advantages which are attained by the invention will become more fully apparent as the description which now follows is read in conjunction with the accompanying drawings.

DESCRIPTION OF THE DRAWINGS

FIG. 1 is a plan view, on a larger than true-life scale, illustrating a preferred embodiment of an orthodontic product constructed in accordance with the present invention.

FIG. 2 is an enlarged fragmentary and partially cross-sectioned view illustrating the left end of the product shown in FIG. 1.

FIG. 3 is a fragmentary view, on a slightly smaller than true-life scale, illustrating how the apparatus of the invention may be held in a person's hand to facilitate initial replacement of a tension-applying device.

FIG. 4 is a fragmentary side elevation, on about the same scale as FIG. 1, illustrating an actual in-the-mouth manipulation using the apparatus of the invention.

DETAILED DESCRIPTION OF THE INVENTION

Turning now to the drawings, and referring first to FIGS. 1 and 2, indicated generally at 10 is an orthodontic product constructed in accordance with the present invention. Included in product 10 is a molded elastomeric body 12 including a central ring 12a, and a pair of diametrically outwardly opposing elongated fingers 12b, 12c. Ring 12a, and fingers 12b, 12c, are referred to herein as a carrier.

Molded integrally with fingers 12b, 12c, at locations such as those shown in these figures, are plural orthodontic intraoral tension-applying devices, such as devices 14. As can be seen, devices 14 herein have elongated configurations, with each including, adjacent its opposite ends, a pair of eyelets, such as eyelets 14a, 14b, joined by an elongated strand, such as strands 14c.

The molded portions of product 10, which have just been illustrated, are prepared in such a way that each of the tension-applying devices is joined to a finger through what is referred to herein as a break-away isthmus, which is a relatively small cross-section region of material that enables each tension-applying device easily to be severed, as by snap action, from its associated finger. Thus, the product acts as a carrier for the very devices which it is adapted to dispense, and as will be explained, to aid in installing.

With regard to the apparatus as so far described, an early relative of this kind of device is fully described and shown in a prior patent, issued to Paul E. Klein on Aug. 2, 1977, U.S. Pat. No. 4,038,753, entitled "Orthodontic Apparatus Including Unitary Dispenser and Dispensed Articles". Here, as there, the molded portions of apparatus 10 are formed of a commercially available, thermoset-thermoplastic, polyester-based, isocyanate-terminated urethane resin.

The kind of tension-applying device which is employed in apparatus 10 herein is employed to produce orthodontic corrective tension forces between a pair of relatively widely spaced points in a person's mouth. It is for this reason that devices carried in apparatus 10 have the shapes shown for them in the figures, as just described above.

Included in apparatus 10, according to an important feature of the invention, with respect to each of fingers 12b, 12c, is an elongated relatively rigid reversely bent catch, such as the catches shown at 16, 18 for fingers 12b, 12c, respectively. Each of these catches has substantially the same configuration, with each formed of a steel wire having about the same cross-sectional and strength characteristics as wire which is used in conventional so-called paper clips. As can be seen, each end of each catch has a curl or a reverse bend in it, with the inner end of each catch embedded in the material forming the associated supporting finger. More specifically, catch 16 has an outer reverse bend 16a and an inner reverse bend 16b—the latter being embedded, as shown, adjacent the outer end of finger 12b. Similarly, catch 18 includes an outer reverse bend 18a, and an inner reverse bend 18b which is embedded, as shown, adjacent the outer end of finger 12c.

FIG. 1 illustrates apparatus constructed according to the invention essentially in the unchanged condition which it would typically have when given by an orthodontist to a patient departing his office. In the particular device illustrated, the same includes twenty dispensable tension-applying devices. This number is, of course, in no way critical.

FIGS. 3 and 4 in the application illustrate a typical procedure for using the apparatus of the invention. It should be understood that, with respect to the device or devices which the orthodontist has indicated will require replacement, he will normally have supplied a patient with a product 10 which carries tension-applying devices substantially the same as the as the one or ones which he, the orthodontist, has initially installed.

When it is desired to make a replacement, the user simply severs, as by snapping, a tension-applying device, and loops one of its eyelets over the curved end in one of catches 16, 18. Referring to FIG. 3, it will be seen that one of the tension-applying devices has indeed been severed from finger 12c, with an end of the device being looped on the curved end portion of catch 16. FIG. 3 illustrates a typical manner in which a right-handed patient would grasp the apparatus thereafter to use it as a tool for installing the just-severed tension-applying device. If it is desired to steady the about-to-be-installed tension-applying device against free dangling, the thumb and forefinger would typically be slid forwardly to grasp that end of the device which is caught on catch 16.

The device is then manipulated into the person's mouth, with its free eyelet end thereafter caught over one of the two hooks between which the device is intended to act. Referring to FIG. 4, here there is illustrated, in a left-side fragmentary view, a person's upper and lower jaws, 20, 22, respectively, showing an upper-jaw overbite. Provided on one of the rear teeth in the lower jaw is a tooth band 24 which carries a hook 26, which is one of the hooks intended to receive an eyelet in device 14. And, in FIG. 4, a stage in installation has been shown which immediately follows initial catching of the outer free eyelet end of device 14 with hook 26. Through pulling on ring 12, and hence on finger 12b, the about-to-be-installed tension-applying device is stretched as shown in FIG. 4, until its eyelet end which is now caught by catch 16 is adjacent the other hook in a person's mouth whereon it is to be hooked. Such a hook is shown at 28 mounted on a tooth band 30 anchored adjacent one of the patient's upper front teeth.

When the newly installed tension-applying device is properly in place, the curved outer end of catch 16 is removed from the eyelet which it previously held, and apparatus 10 is retired to some suitable storage location until it is again needed.

The advantages and conveniences offered by the apparatus of the invention, which features were mentioned earlier, are now believed to be apparent. And, while a preferred embodiment of this invention has been shown and described herein, it is appreciated that changes and modifications may be made without departing from the spirit of the invention.

It is claimed and desired to secure as Letters Patent:

1. Orthodontic apparatus usable by a patient wearing orthodontic hardware of the type including a pair of spaced hook-like elements to place tension between such elements, said apparatus comprising:

an elastomeric digitally manipulatable carrier portion including at least one elongated flexible projecting finger, a plurality of elastomeric intraoral orthodontic devices severably joined to and integral with the finger in said carrier portion, each device including at least a pair of operatively interconnected endless loops or the like, and a relatively rigid reverse-bend catch joined to and projecting axially from the outer end of said finger for receiving releasably a selected loop in a device severed from said carrier thus to enable maneuvering of the severed device, through maneuvering of said catch, adjacent and within a person's mouth to place one loop in the device in a caught relationship over one of such hook-like elements, and another loop in the device in a caught relationship over the other element.

2. Orthodontic apparatus usable by a patient wearing orthodontic hardware of the type including a pair of spaced hook-like elements to place tension between such elements, said apparatus comprising an elastomeric digitally manipulatable carrier portion including an elongated outwardly projecting finger-like portion having inner and outer ends, a plurality of elongated elastomeric intraoral orthodontic devices severably joined to and integral with said finger-like portion, each device including at least a pair of operatively interconnected endless loops or the like, and a relatively rigid reverse-bend elongated catch joined to and projecting axially outwardly from the outer end of said finger-like portion for receiving releasably a selected loop in a device severed from said carrier, thus to enable maneuvering of the severed device, through maneuvering of said finger portion and said catch, adjacent and within a person's mouth to place one loop in the device in a caught relationship over one of such hook-like elements, and another loop in the device in a caught relationship over the other element.

* * * * *